United States Patent [19]

Wright et al.

[11] Patent Number: 4,861,907

[45] Date of Patent: Aug. 29, 1989

[54] PROCESS FOR SYNTHESIS OF ACYLAMINO SILICON COMPOUNDS

[75] Inventors: Antony P. Wright, Rhodes; David J. Bunge, Midland, both of Mich.

[73] Assignee: Dow Corning Corporation, Midland, Mich.

[21] Appl. No.: 335,612

[22] Filed: Apr. 10, 1989

[51] Int. Cl.$^4$ .............................................. C07F 7/10
[52] U.S. Cl. .................................................... 556/419
[58] Field of Search ....................................... 556/419

[56] References Cited

U.S. PATENT DOCUMENTS 2,929,829  3/1960  Morehouse ......................... 556/419
4,507,455  3/1985  Tangney et al. ................. 556/419 X
4,608,270  8/1986  Varaprath ......................... 556/419 X
4,788,310  11/1988  Stein et al. ........................... 556/419

Primary Examiner—Paul F. Shaver
Attorney, Agent, or Firm—Killworth, Gottman, Hagan & Schaeff

[57] ABSTRACT

Organosilicon compounds containing at least one acylamino-substituted hydrocarbon radical are prepared by reacting an organosilicon compound containing at least one amino-substituted hydrocarbon radical with an acyl halide in a nonaqueous solvent in the presence of an aqueous alkaline material and an additive that facilitates the transfer of the alkaline material into the nonaqueous phase.

28 Claims, No Drawings

PROCESS FOR SYNTHESIS OF ACYLAMINO SILICON COMPOUNDS

BACKGROUND OF THE INVENTION

This invention relates generally to a method for preparing organosilicon compounds that contain silicon-bonded acylamino-substituted hydrocarbon radicals. More specifically, the method involves the reaction of aminoalkylsilanes and siloxanes with acyl halides in nonaqueous media in the presence of an aqueous acid acceptor with an additive to facilitate the phase transfer of the acid acceptor into the nonaqueous phase.

Organosilicon compounds that contain silicon-bonded acylamino-substituted hydrocarbon radicals are well known and have been described in U.S. Pat. No. 4,608,270 which is herein incorporated by reference.

As mentioned in Varaprath U.S. Pat. No. 4,608,270 and as taught in U.S. Pat. No. 2,929,829 to Morehouse, Japan 51/108022 to Furuya et al., Japan 56/74113 to Takamizawa and West German DE No. 2365272 to Koetzsch et al., acylaminoorganopolysiloxanes can be synthesized by reacting aminosiloxanes with the corresponding acid chloride in the presence of a tertiary amine such as triethylamine. However, such a synthesis has several disadvantages. First, the removal of the voluminous precipitate of triethylamine hydrochloride by filtration is tedious. Second, a small amount of HCl is liberated even when an excess of amine is used. This HCl is detrimental to the stability of the polymer, especially when the acid chloride has other reactive vinyl functionality such as where the acid chloride is acryl chloride.

An alternative method for the preparation for the acylaminoorganopolysiloxanes involves the reaction of aminosiloxanes and silanes with an acid anhydride or ester at elevated temperature. This is taught in U.S. Pat. No. 4,507,455 to Tangney and Ziemelis, assigned to the assignee of the present invention. Unfortunately at the elevated temperatures of the reaction, arcylamide derivatives undergo Michael addition and amidation of the acrylic double bond resulting in unwanted by-products and crosslinkage of the desired product which ultimately causes the polymer to gel.

Finally as taught in the above-mentioned U.S. Pat. No. 4,608,270 to Varaprath, these problems can be overcome by reacting the aminosilanes and siloxanes with acid chlorides in the presence of aqueous sodium hydroxide. The HCl that is produced on addition of acyl chloride is neutralized by hydroxide in the aqueous phase. However, a problem arises from the fact that this reaction is carried out in a two-phase system in which the aminosiloxane is dissolved in an organic solvent that is immiscible with water. Because the amide function is generally highly polar and hydrophilic, it shows a great tendency to absorb moisture. Incorporation of these units into the siloxane backbone increases water miscibility causing the polymers to emulsify easily thus making phase separation difficult. To some extent, this problem can be overcome by using chlorinated solvents such as methylene chloride or chloroform but, unfortunately, such solvents are toxic.

It is thought that these solvents are effective because they typically contain substantial amounts, such as greater than 0.05 weight percent at ambient conditions, of dissolved water which serves to assist in the phase transfer of chloride ion byproduct from the nonaqueous to the aqueous phase.

Attempts to use non-toxic solvents other than chlorinated solvents have lead to gellation, poor conversion to product or poor phase separation.

Accordingly, the need remains for an improved method for preparing acylaminoorganosilicon compounds that avoids the phase separation and solvent toxicity problems previously encountered while simultaneously providing transfer of acid acceptor and salt by-product across the interface of a two-phase system.

BRIEF SUMMARY OF THE INVENTION

This need is met by the present invention which is directed to a method for preparing organosilicon compounds that contain at least one silicon-bonded acylamino-substituted hydrocarbon radical using a two-phase solvent system and an additive to facilitate transfer of an acid acceptor from the aqueous to the nonaqueous phase. The additive provides an additional degree of freedom to adjust the solubility of water in the nonaqueous phase. Preferably, an aminosilicon compound, that is, an aminosilicon compound having at least one silicon-bonded amino-substituted hydrocarbon radical containing at least one nitrogen-bonded hydrogen, is reacted with an acyl halide in a nonaqueous and non-toxic solvent such as hexane in the presence of an aqueous solution of an acid acceptor, e.g., an alkaline material such as sodium hydroxide. The silicon-bonded amino-substituted hydrocarbon radical preferably has the formula $-Q(NHQ')_aNZH$ wherein Q and Q' are divalent hydrocarbon radicals, Z is a hydrogen atom or a substituted or unsubstituted monovalent hydrocarbon radical, and "a" is 0 or 1. An additive such as methanol or tetrahydrofuran that is compatible with both phases is used to facilitate the transfer of the acid acceptor into the nonaqueous phase and neutralize the HCl that is produced in the primary reaction. Preferably the reaction is carried out at a temperature of about 0 to 10° C. when acrylyl halides are used in order to minimize side reactions.

The present process provides an efficient and economical system for producing acylamino organosilicon compounds. It utilizes an easy to handle alkaline material without phase separation problems. For aminosilicon compounds with an amine neutral equivalent of about 800 or higher, phase separation to a clear lower phase and a slightly translucent upper phase with a sharp phase boundary takes less than a few hours. Left overnight, the top phase also becomes perfectly clear. Use of filter presses and other separation and/or clarification techniques are not required.

If the reaction is controlled properly, no methyl acylate will be formed. Because no methyl acylate is found, it is possible to recycle the solvent. Likewise, the waste product, i.e., a salt (for example NaCl) solution, is easily collected and disposed of. All this makes it possible to use the present process continuously with low energy input and high yield product output.

Thus an improved process without many of the drawbacks of the prior art is provided for producing acylamino organosilicon compounds. As described in the Varaprath U.S. Pat. No. 4,608,270, the acylamino organosilicon products are useful for paper release coatings and conformal coatings.

Accordingly, it is an object of the present invention to provide an improved method for preparing organosilicon compounds that contain silicon-bonded acylamino-substituted hydrocarbon radicals of the type described in the Varaprath U.S. Pat. No. 4,608,270. These and other objects of and advantages of the invention will become apparent from the following description and the appended claims.

DETAILED DESCRIPTION OF THE INVENTION

The preferred method consists of reacting an acyl halide with an aminosilicon compound having at least one silicon-bonded amino-substituted hydrocarbon radical containing at least on nitrogen-bonded hydrogen. The remaining silicon bonds are satisfied with organic radicals or divalent, silicon-linking, oxygen atoms, or both. The improved reaction of the present invention is carried out in the presence of an aqueous solution of an acid acceptor, e.g., an alkaline material, and a small amount of additive to facilitate the transfer of the acid acceptor into the nonaqueous phase.

Typically the aminosilicon compound, a nonaqueous solvent, an aqueous solution of the alkaline material, and a small amount of additive are mixed together. An acyl halide is dissolved in the nonaqueous solvent and gradually added to the mixture. After the addition is complete, the resulting mixture is agitated until the reaction is complete. The mixture is allowed to stand until the aqueous and nonaqueous phases separate after which the nonaqueous phase is split off and the nonaqueous solvent stripped of the resulting product.

The aminosilicon compound that is to be acylated can have any structure as long as it contains at least one silicon atom bonded to an amino-substituted hydrocarbon radical that bears one or more amino radicals at least one of which has a nitrogen-bonded hydrogen atom. The other silicon bonds are satisfied by organic radicals other than amino-substituted hydrocarbon radicals noted above or by divalent, silicon-linking oxygen atoms. Thus the aminosilicon compound can be a silane, a siloxane, a silcarbane, or a silcarbanesiloxane.

The silicon-bonded amino-substituted hydrocarbon radical has the formula —Q(NHQ')$_a$NHZ where Q and Q' denote divalent hydrocarbon radicals, Z denotes a hydrogen atom or a monovalent hydrocarbon radical, i.e., an R radical, and "a" has a value of 0 or 1.

Examples of Q radicals and Q' radicals include, but are not limited to, alkylene radicals such as ethylene, propylene, isopropylene, butylene, isobutylene, hexylene, octylene and arylene radicals such as phenylene, xylylene, etc. Q is preferably ethylene and Q' is preferably propylene or isobutylene.

Examples of Z hydrocarbon radicals (R radicals) include, but are not limited to, alkyl radicals such as methyl, ethyl, propyl, butyl, hexyl, and octyl; cycloaliphatic radicals such as cyclohexyl; aryl radicals such as phenyl, benzyl, styryl, tolyl, and xenyl; and alkenyl radicals such as vinyl and allyl.

Thus, examples of amino-substituted hydrocarbon radicals include, but are not limited to, $NH_2CH_2CH_2CH_2$—, $CH_2NHCH_2CH_2CH_2$—, $NH_2CH_2CH(CH_3)CH_2$—, $NH_2CH_2CH_2NHCH_2CH_2CH_2$—, $NH_2CH_2CH_2NHCH_2CH(CH_3)CH_2$—, $NH_2(CH_2)_6NH(CH_2)_3$—, and $NH_2(CH_2)_6NHCH_2CH(CH_3)CH_2$—.

Silicon-bonded radicals, other than the above-noted amino-substituted hydrocarbon radicals, include organic radicals and divalent, silicon-linking, oxygen atoms. Examples of said organic radicals include, but are not limited to, divalent, silicon-linking hydrocarbon radicals such as the Q and Q' radicals noted above, and halogenated derivatives thereof, monovalent hydrocarbon radicals such as the R radicals noted above, and halogenated derivatives thereof, and hydrogen atoms. Preferably said organic radicals contain no more than 6 carbon atoms, such as methyl, 3,3,3-trifluoropropyl, phenyl and vinyl radicals, and most preferably are methyl radicals.

The aminosilicon compounds to be acylated by the process of this invention are preferably silanes or siloxanes having the average formula $R_c(NH_2(Q'NH)_aQ)_dSiO_{4-c-d)/2}$ where "a" has a value of 0 or 1, "c" denotes a number having a value of from 0 to 3, such as 0, 0.5, 1.01, 2, 2.1, and 3, "d" denotes a number having a value of from >0 to 4, such as 0.01, 0.5, 1, 2, and 3, and "c"+"d" has a value of from 1 to 4 such as 1.5, 1.99, 2.01, 3, and 4. Of course, the aminosilane or siloxane must contain an average of at least one silicon-bonded, amine-substituted hydrocarbon radical per molecule. The siloxanes can contain siloxane units that are free of amino-substituted hydrocarbon radicals such as $R_cSiO_{4-c)/2}$, e.g., $MeSiO_{3/2}$, $Me_2SiO_{2/2}$, $Me_3SiO_{1/2}$, $MeViSiO_{2/2}$, $ViMe_2SiO_{1/2}$, and $SiO_{4/2}$ units, in addition to siloxane units that contain the required amino-substituted hydrocarbon radicals. Herein the symbols Me and Vi denote methyl and vinyl, respectively.

Preferred aminosilanes to be acylated have the formula $R_eSi(QNHCH_2CH_2HN_2)_{4-e}$ where "e" denotes a number having a value of 0, 1, 2, or 3, as for example, $Me_3SiCH_2CH(CH_3)CH_2NHCH_2CH_2NH_2$.

Preferred aminosiloxanes to be acylated have the formula $YR_2SiO(R_2SiO)_x(YRSiO)_ySiR_2Y$ where each Y denotes, independently, an R radical or a —$QNHCH_2CH_2NH_2$ radical and x and y denote numbers having average values of from 0 to 5000 and 0 to 500, respectively. Examples of preferred aminosiloxanes to be acylated include, but are not limited to, $Me_3SiO(Me_2SiO)_{500}(MeYSiO)_2SiMe_3$, $YMe_2SiO(Me_2SiO)_{2000}SiMe_2Y$, $YMe_2SiO(Me_2SiO)_{100}(MeYSiO)_3SiMe_2Y$, $Me_3SiO(MeYSiO)_1SiMe_3$, and $YMe_2SiO(MeYSiO)_1SiMe_2Y$.

Aminosiloxanes can also have a cyclic or branched structure, such as $(YMe_2SiO)_4Si$ and $(YMeSiO)_4$, in addition to the linear structures noted above.

Aminosilicon compounds and their preparation are well known in the organosilicon art. Some are commercially available. The disclosures of U.S. Pat. Nos. 2,557,803, 2,738,357, 2,754,312, 2,762,823, 2998,406, 3,045,036, 3,087,909, 3,355,424, 3,560,543, 3,890,269, 4,036,868, 4,152,346, and 4,507,455 are incorporated herein by reference to further teach how to prepare aminosilicon compounds that can be used in the method of this invention.

The acyl halide can have any structure such as a linear, branched, or cyclic structure having aromatic, heterocyclic, olefinic or paraffinic bonding and containing one or more carbon-bonded —COX radicals, where X denotes a halogen atom. Preferably the acyl halide has the structure R'COX Where X denotes a halogen atom, preferably chlorine, and R' denotes a substituted or unsubstituted monovalent hydrocarbon radical.

Examples of unsubstituted monovalent hydrocarbon radicals include, but are not limited to, those delineated above. Examples of corresponding acyl halides include acetyl chloride, benzoyl chloride and, most preferably, acrylyl chloride, methacrylyl chloride, and cinnamoyl chloride.

Examples of substituted monovalent hydrocarbon radicals include, but are not limited to, halogenated monovalent hydrocarbon radicals such as —CF$_3$, and —C$_6$H$_4$Cl, and other substituted radicals which are stable under the reaction conditions employed in the method of this invention such as —CH$_2$CH$_2$CN, —C$_6$H$_4$NO$_2$ and —C(CN)=CH$_2$.

The acyl halide is added to a mixture of an aminosilicon compound, a nonaqueous solvent, an aqueous solution of an alkaline material, and a small amount of additive at least partially soluble in both the nonaqueous and aqueous phases. In the absence of this additive gellation of the reaction mixture occurs during, or shortly after, the reaction. Preferably, the additive should have a solubility of more than about 2.5 weight percent in both the nonaqueous and aqueous phases. Preferably, additives such as methanol, ethanol, propanol, tetrahydrofuran, dioxane, and dimethoxyethane are used. Preferably, when alcohol additives such as methanol are used, the amount of additive should be kept to a low level. Preferred are amounts in the range of 0.25–25.0 g of methanol additive for every 50 g of aminosilicon compound and most preferably around 1.5 g/50 g. This converts to a weight percent range of 0.5 to 50, and most preferably around 3 percent. Within this range, it has been found that while larger amounts of additive are workable, long term stability of the resulting acrylamino organosilic on compound may be impaired. This is believed to be due to the fact that in order to obtain an acrylamidoalkylpolysiloxane with a long term stable viscosity, it is desirable to convert a higher percentage (>95%) of amine to amide. When a large amount of methanol additive is used, the conversions go down. For example, 10 weight percent gives around a 91% conversion, and 20 weight percent gives around a 90% conversion. This is apparently due to the occurrence of competing reactions such as formation of methyl acrylate, which are facilitated in the presence of an excess of additive. Thus in order to maximize amide formation and to minimize side reactions, it is desirable to reduce the concentration of methanol to the lower range levels. Other additives are not so limited. Thus, side reactions can also be avoided by using an additive such as tetrahydrofuran.

A nonaqueous solvent is used to dissolve the aminosilicon compound and the acyl halide to be added to it. The nonaqueous solvent can be any suitable, substantially water-insoluble liquid that dissolves substantially no water and will not react with the components of the reaction but will facilitate phase separation. The nonaqueous solvents that are used in the process of this invention exclude those which, in the pure state, dissolve more than 0.05 percent by weight of water at 25° C. and atmospheric pressure. Preferably the solvent is also a solvent for the organosilicon product of the reaction. Generally polar solvents that are capable of dissolving substantial amounts of water, e.g., ethyl acetate or diethyl ether, may result in too much water in the nonaqueous phase, especially when used in conjunction with an additive. When too much water is present, hydrolysis of the acyl halide takes place and salts are retained in the nonaqueous phase which precipitate on stripping of the organic phase from the product mixture. Oxygen containing solvents are not as suitable since they can form hydroperoxides that gel the acrylamide products. Esters can hydrolyse under the basic conditions of the reaction.

While not wishing to limit this invention by theory we postulate that the function of the additive is to provide the proper amount of water in the nonaqueous phase so as to facilitate mass transfer of amine hydrochloride intermediate to the organic/aqueous phase boundary or mass transfer of alkaline material from the aqueous phase to the organic phase. The amount of the additive can be adjusted to optimize these processes and thus provide a maximum conversion of amine to amide.

The nonaqueous solvent should have a density that is significantly higher or lower than the aqueous solution of by-product salt in order to facilitate phase separation. The nonaqueous solvent should have a boiling point preferably below 120° C. and most preferably below 90° C. so that it can be vacuum stripped from the product at temperatures below 100° C. Examples of suitable solvents include, but are not limited to, hydrocarbons such as hexane, hexene, cyclohexane and heptane and isomers thereof including mixtures of such solvents such as petroleum ether. Preferably a non-toxic and non-aromatic solvent such as hexane is used. The amount of solvent that is used should be sufficient to dissolve the aminosilicon compound and, preferably, the organosilicon product as well.

When reacting acryl halides with aminosilicon compounds with high amine functionality, there is a tendency for the acrylamide polymer product to act like a surfactant and afford poor phase separation. Thus when aminosilicon compounds with an amine neutral equivalent below about 800 are reacted with acrylyl chloride in a hexane/aqueous sodium hydroxide solution using methanol as an additive, emulsions tend to form. However, in some instances this can be put to good use since such emulsions are suitable for use in formulations such as those found in hair care products.

The necessary components of the reaction mixture, i.e., the acyl halide, the aminosilicon compound, nonaqueous solvent, aqueous solution of alkaline material and additive can be mixed in any manner as long as the acyl halide is added to the aminosilicon compound in the presence of the nonaqueous solvent, the aqueous solution of alkaline material, and the additive. In a preferred embodiment, the acyl halide or a solution thereof is added to a well agitated mixture of a nonaqueous solution of the aminosilicon material, the aqueous solution of alkaline material, and the additive.

The alkaline material can be any material that will react with hydrochloride. Preferred alkaline materials include NaOH, KOH and LiOH, although it is thought that Ba(OH)$_2$ would also be suitable. Less suitable alkaline materials include weak bases such as Na$_2$CO$_3$ and NaHCO$_3$.

Since acyl halides react with methanol to form esters, a 10% excess of acyl chloride based on the amine content is preferably used for the reaction. A deficiency of acyl halide relative to the total number of acylatable amino groups, although merely leading to the preparation of incompletely acylated product when the acyl halide is free of aliphatic unsaturation, leads to products which can undergo a Michael-Addition type reaction when the acyl halide contains aliphatic unsaturation. For this reason, it is preferred, although not required, to fully acrylate the aminosilicon compound when an acrylyl halide is used. A slight excess (3–5%) of acyl chloride over sodium hydroxide is preferably used. By using an indicator such as phenolphthalein, a change in color indicates that the alkaline material has been completely neutralized. A deficiency of alkaline material relative to the amount of hydrogen halide produced is to be avoided. The concentration of alkaline material, preferably sodium hydroxide, in the aqueous phase should be kept as high as possible in order to achieve a high concentration of sodium chloride on reaction of the alkaline material with the hydrogen chloride formed in the primary reaction. Sodium hydroxide concentrations above 2.0N should be used with a concentration of about 2.5N being preferred. The resulting concentrated aqueous solution of sodium chloride is effective in clearing the nonaqueous phase of cloudiness. Concentrations of sodium chloride above about 2.5N result in unwanted separation of solid sodium chloride from the reaction solution.

Except when the acyl halide is an acrylyl halide, the method of this invention can be practiced at any reasonable temperature. Advantageously this method proceeds readily at room temperature. When acrylyl halide is used, this method should be practiced at as low a temperature as possible to minimize the formation of by-products. Accordingly, when using the method of this invention to prepare acrylyl-substituted aminosilicon compounds, the reaction should be carried out at a temperature of about 0° to 10° C. Lower reaction temperatures are suitable provided the water does not freeze; higher reaction temperatures substantially reduce the yield of desired product.

During and after the addition of the acyl halide component to the aminosilicon component, the reaction mixture should be thoroughly agitated to maintain an intimate contact between the alkaline material and the hydrogen chloride reaction product. The usual low shear means such as stirrers, paddles, and impellers are sufficient to maintain sufficient agitation. Agitation is maintained until the acylation reaction is finished, typically within an hour.

After the reaction is finished, the product of the reaction can be separated by allowing the aqueous and nonaqueous phases to separate. The phases are split and the nonaqueous product-containing phase stripped of solvent. When acrylyl-substituted products are to be separated from the solvent, it is desirable to add a polymerization inhibitor such as sodium nitrite to the solution prior to any separating action such as distilling or fractionation.

The reaction can also be carried out as a continuous process. A metered amount of the aqueous base, nonaqueous solvent, additive, and amino silicon compound is combined with a metered amount of the acyl chloride and allowed to remain in contact for about 20 min. Phase separation of the resulting solution takes place in a holding tank overnight. No filtration is required. Solvent recycling is convenient, especially when low boiling solvents such as hexane are used. The concentrated sodium chloride solution is also easy to dispose of.

The products of this method are useful as polar silicon-containing additives for cosmetic compositions, coating compositions, textile treating compositions, and paints. The compositions are useful as comonomers with polymerizable vinyl monomers such as styrene, methyl methacrylate, ethyl acrylate, vinyl acetate, vinyl chloride, vinylidene chloride and acrylonitrile. In particular the compounds having acrylylamine-substituted hydrocarbon radicals are useful as a reactive component in free radical curable compositions such as radiation curable compositions used for paper, resin protective, and optical fiber coatings.

The following examples are disclosed to further teach the practice of the invention and are not intended to limit the invention as it is delineated in the claims.

EXAMPLE 1

A one liter, three-necked flask equipped with a thermometer, stirring paddle, airtight stirring sleeve, $N_2$ inlet and dropping funnel was charged with $YMe_2SiO(Me_2SiO)_{98}SiMe_2Y$ where Y is $-CH_2CH(CH_3)CH_2NHCH_2CH_2NH_2$ (50.0 g, 0.0250 moles), hexane (80.0 g; 2.469N sodium hydroxide solution in water (11.1 g; 0.0275 moles), methanol (1.5 g) and 0.9 g 15% sodium nitrite solution in water. The mixture was stirred under $N_2$ atmosphere and cooled to 0° C. using a dry ice/isopropanol bath. Three drops of 1% phenolphthalein solution in ethanol added to the flask as an acid/base indicator. To this, 2.6 g (0.0285 moles) of acrylyl chloride dissolved in 20 g of hexane in and addition funnel wa s added gradually over a period of 30 minutes. The mixture was agitated for another 20 minutes. The cooling bath was removed and, after 5 minutes, the solution in the flask went from pink to colorless indicating all the sodium hydroxide had been neutralized. The mixture was transferred to a separatory funnel where, after 16 hours, good phase separation had occurred. The phases were split and the hexane solvent was removed under reduced pressure. The product had a viscosity of 1439 cs at 25° C. An amine neutral equivalent was determined by titrating the sample in glacial acetic acid using methyl violet as an indicator. Indicator interference from sodium nitrite can be eliminated by adding three drops of 30% hydrogen peroxide to the polymer acetic acid mixture one minute prior to addition of the nndicator. An amine neutral equivalent of 38412 grams per equivalent nitrogen indicated a conversion of more than 94.8% amine functionality to acrylamide. When the sample was treated with acetic anhydride or methyl iodide (compounds shown to remove amines from the system) prior to titration, the titration value did not change indicating that the residual materials was not amine but probably sodium acrylate. With all other reaction parameters the same, respective yields of 90.7% and 90.3% were obtained when 5.0 and 10.0 g of methanol additive were used. When no methanol additive was used, the reaction mixture gelled shortly after half of the acrylyl chloride solution had been added.

EXAMPLE 2

The procedure of Example 1 was used except that 5 ml of tetrahydrofuran was substituted for 1.5 ml of methanol. The phase separation was slightly cleaner with a very sharp phase boundary. An amine neutral equivalent of 78994 grams per equivalent nitrogen indicated a 97.5% conversion.

EXAMPLE 3

Sodium hydroxide (2.5N; 11.2 parts) was metered with 100 parts hexane containing 5 parts tetrahydrofuran and 50 parts of $YMe_2SiO(Me_2SiO)_{98}SiMe_2Y$ where Y is $-CH_2CH(CH_3)CH_2NHCH_2CH_2NH_2$ and 2.58 parts of acrylyl chloride. A 20 minute residence time was sufficient. Phase separation to a clear lower phase and slightly translucent upper phase with a sharp phase boundary was complete in less than 1.5 hrs. The top phase became clear on sitting in a holding tank overnight. The yield was 97.5%.

That which is claimed is:

1. A method for preparing an organosilicon compound containing at least one silicon-bonded acylamino-substituted hydrocarbon radical comprising reacting an acyl halide with an aminosilicon compound having at least one silicon-bonded amino-substituted hydrocarbon radical containing at least one nitrogen-bonded hydrogen, all other silicon valences therein being satisfied by radicals selected from the group consisting of organic radicals and divalent, silicon-linking, oxygen atoms, in a nonaqueous solvent in the presence of an aqueous solution of a watersoluble acid acceptor and an additive that promotes transfer of said acid acceptor from said aqueous solution to said nonaqueous solvent and is at least partially soluble in both said aqueous solution and nonaqueous solvent.

2. The method according to claim 1 wherein said silicon-bonded amino-substituted hydrocarbon radical has the formula —$Q(NHQ')_aNZH$ and said acyl halide has the formula $R'COX$, wherein Q and Q' denote divalent hydrocarbon radicals, R" denotes a substituted or unsubstituted monovalent hydrocarbon radical, X denotes a halogen atom, Z denotes a hydrogen or a monovalent hydrocarbon radical, and "a" has a value of 0 or 1.

3. A method according to claim 2 wherein said acyl halide is a compound selected from the group consisting of $CH_2=CHCOCl$, $CH_2=C(CH_3)COCl$, and $C_6H_5CH=CHCOCl$.

4. A method according to claim 3 wherein said aminosilicon compound has the average unit formula $R_c(NH_2(Q'NH)_aQ)_dSiO_{(4-c-d)/2}$ wherein R denotes a monovalent hydrocarbon radical, "a" has a value of 0 or 1, "c" has a value of from 0 to 3, "d" has a value of >0 to 4, and "c"+"d" has a value of 1 to 4.

5. A method according to claim 4 wherein said aminosilicon compound is a siloxane have the formula $YR_2SiO(R_2SiO)_x(YRSiO)_ySiR_2Y$ wherein Y denotes R or —$QNHCH_2CH_2NH_2$, x has a value of from 0 to 5000, and y has a value of from 0 to 500.

6. A method according to claim 4 wherein said aminosilicon compound is a silane having the formula $R_eSi(QNHCH_2CH_2HN_2)_{4-e}$ wherein e has a value of 0, 1, 2, or 3.

7. A method according to claim 4 wherein R is selected from the group consisting of methyl, phenyl and vinyl.

8. A method according to claim 1 wherein said acyl halide is added to a mixture of said aminosilicon compound and a nonaqueous solvent therefore, said acid acceptor and said aqueous solvent therefore, and said additive.

9. A method according to claim 8 wherein the resulting mixture obtained by adding said acyl halide is thereafter agitated until said organosilicon compound containing at least one silicon-bonded acylamino-substituted hydrocarbon radical is formed.

10. A method according to claim 1 further comprising isolating said organosilicon compound containing at least one silicon-bonded acylamino-substituted hydrocarbon radical.

11. A method according to claim 1 wherein said reaction is carried out at a temperature of from 0 to 10° C.

12. A method according to claim 1 wherein said acid acceptor is an alkaline material.

13. A method according to claim 12 wherein said alkaline material is an alkali metal hydroxide.

14. A method according to claim 13 wherein said alkali metal hydroxide is sodium hydroxide.

15. A method according to claim 1 wherein said nonaqueous solvent is a water insoluble liquid.

16. A method according to claim 15 wherein said water insoluble liquid is a hydrocarbon solvent.

17. A method according to claim 16 wherein said hydrocarbon solvent is hexane.

18. A method according to claim 1 wherein said additive is an organic compound.

19. A method according to claim 18 wherein said additive has a solubility in both said aqueous solution and said nonaqueous solvent of more than about 2.5 weight percent.

20. A method according to claim 18 wherein said organic compound is selected from the group of alcohols consisting of methanol, ethanol, and propanol.

21. A method according to claim 20 wherein said alcohol is methanol.

22. A method according to claim 21 wherein about 0.25 to 50 g of methanol is used for each 50 g of said aminosilicon compound.

23. A method according to claim 22 wherein about 1.5 g of methanol is used for each 50 g of said aminosilicon compound.

24. A method according to claim 18 wherein said organic compound is selected from the group consisting of tetrahydrofuran, dioxane, and dimethoxyethane.

25. A method according to claim 1 wherein the molar amount of said acyl halide is in about 3.5% molar excess over the equivalent amount of said alkaline material.

26. A method according to claim 1 wherein the molar amount of said acyl halide is in about 10% molar excess over the molar amount of at least one nitrogen-bonded hydrogen atom per molecule of aminosilicon compound.

27. A method according to claim 1 wherein the molar amount of said acyl halide is about 10 times the molar amount of additive.

28. A method according to claim 1 wherein said method is carried out in a continuous process by reacting metered amounts of said aminosilicon compound, solvent, aqueous solution of alkaline material, and additive with a metered amount of said acyl halide.

* * * * *